(12) United States Patent
Plaian

(10) Patent No.: US 8,974,060 B2
(45) Date of Patent: Mar. 10, 2015

(54) LIGHTING DEVICE FOR FUNDUS CAMERAS

(75) Inventor: Andrei Plaian, Ponte San Nicolò (IT)

(73) Assignee: Centervue S.p.A., Padua (IT)

(*) Notice: Subject to any disclaimer, the term of this patent is extended or adjusted under 35 U.S.C. 154(b) by 101 days.

(21) Appl. No.: 13/501,698

(22) PCT Filed: Sep. 30, 2010

(86) PCT No.: PCT/EP2010/064610
§ 371 (c)(1),
(2), (4) Date: May 30, 2012

(87) PCT Pub. No.: WO2011/045190
PCT Pub. Date: Apr. 21, 2011

(65) Prior Publication Data
US 2012/0249960 A1    Oct. 4, 2012

(30) Foreign Application Priority Data
Oct. 13, 2009  (IT) .............................. TV2009A0201

(51) Int. Cl.
| | |
|---|---|
| A61B 3/10 | (2006.01) |
| A61B 3/02 | (2006.01) |
| B60Q 1/26 | (2006.01) |
| F21S 4/00 | (2006.01) |
| F21V 21/00 | (2006.01) |
| A61B 3/12 | (2006.01) |

(52) U.S. Cl.
CPC ........................................ *A61B 3/12* (2013.01)
USPC ....... 351/206; 351/243; 362/227; 362/249.02

(58) Field of Classification Search
USPC ......... 351/200, 205, 206, 221, 222, 243, 246; 353/94, 99, 121; 362/298, 268, 23.07, 362/23.1, 23.14, 612, 613, 227, 249.02
See application file for complete search history.

(56) References Cited

U.S. PATENT DOCUMENTS

2007/0019160 A1*  1/2007  Kleen et al. .................... 351/206
2010/0237359 A1*  9/2010  Cornelissen et al. ........... 257/88

FOREIGN PATENT DOCUMENTS

| EP | 1964511 A1 | 9/2008 |
|---|---|---|
| WO | WO-2006016366 A2 | 2/2006 |

* cited by examiner

*Primary Examiner* — Stephone B Allen
*Assistant Examiner* — Brandi Thomas
(74) *Attorney, Agent, or Firm* — Novak Druce Connolly Bove + Quigg LLP

(57) ABSTRACT

The present invention relates to a lighting device comprising a light concentrator device operatively associated with a light source comprising a plurality of LED devices. The light concentrator device is composed of a solid transparent body comprising: a first surface (51), at which a light input section (5) is defined to receive the light radiation emitted by the light source; and—a second surface (61), at which a light output section (6) is defined to transmit a light beam having a ring shape; and a plurality of protrusions (7) that protrude from said first surface, at said light input section, said protrusions acting as collimation lenses of the light radiation coming from said light source; and—a plurality of reflection surfaces (8, 9) of the light radiation received from said light input section, said protrusions and said reflection surfaces being mutually positioned so as to convey the light radiation coming from said light source along a predefined path, which extends internally to said transparent body, between said light input section and said light output section.

20 Claims, 9 Drawing Sheets

LIGHTING DEVICE FOR FUNDUS CAMERAS

CROSS REFERENCE TO RELATED APPLICATIONS

This application is a National Phase filing under 35 U.S.C. §371 of PCT/EP2010/064610 filed on Sep. 30, 2010; and this application claims priority to Application No. TV2009A000201 filed in Italy on Oct. 13, 2009 under 35 U.S.C. §119; the entire contents of all are hereby incorporated by reference.

The present invention relates to the field of fundus cameras. In particular, the present invention relates to a lighting device for fundus cameras.

The use of apparatuses for examination of the ocular fundus, commonly defined with the term fundus cameras, is widely known.

These apparatuses optically conjugate the pupil of the eye with a ring light source: the eye is illuminated by a light beam which has a ring section at the level of the pupil and the light reflected from the retina is collected through the central portion of the pupil to observe or photograph the retina.

However, a spatial separation exists between the light beam and the beam reflected from the ocular fundus, which is necessary to eliminate or reduce any disturbances deriving from phenomena of light reflection or scattering in the subsequent layers of the eye it passes through.

In fact, these disturbances could greatly compromise the quality of the observation and of the images obtained.

Figure 1:
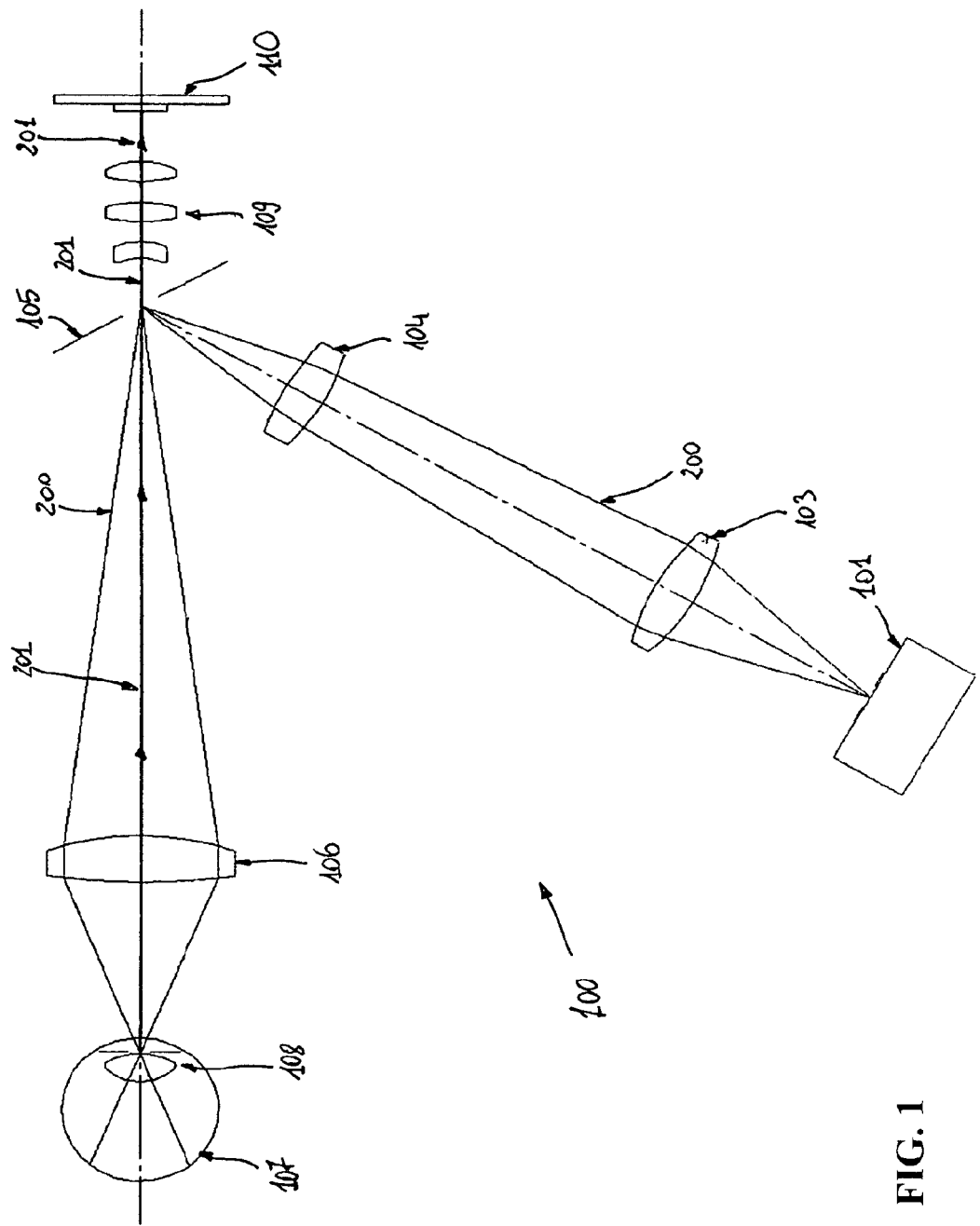

FIG. 1 schematically represents a fundus camera 100 of known type.

A light beam 200, ring shaped, is emitted by an illuminator 1010 and is collimated with a system of lenses 103-104 towards a region comprising the centre of a perforated mirror 105.

The light beam 200 is reflected by the mirror 105 and is directed, through the lens 106, towards the pupil 108 of the patient's eye 107.

The light beam 200 can thus penetrate through a ring section of the pupil 108 and illuminate the ocular fundus.

The light beam 201, reflected from the ocular fundus, passes through the central area of the pupil and is directed, through the lens 106, towards the perforated mirror 105, passing through the hole thereof.

The light beam 201 is then collimated, through a system of lenses 109, towards a sensor 110 which allows an image of the retina to be obtained.

Conventionally, the illuminator 101 is capable of producing the light beam 200, masking the light radiation coming from a light source with a ring diaphragm.

Generally, in a preliminary step of the ocular examination process, the illuminator 101 illuminates the retina with infrared light, given that it is common practice to first observe the ocular fundus, illuminating it by means of non visible light in order to avoid contraction of the pupil, to obtain correct alignment of the whole fundus camera with the eye of the patient.

Illumination with infrared light is followed by flash illumination with white light, of high intensity and very short duration, which allows a colour image of the retina to be obtained.

The illuminator 101 generally comprises an incandescent lamp, operatively associated with appropriate lenses and filters to generate the infrared light and a Xenon tube, to generate the flash of white light.

The conventional lighting devices generally have a relatively bulky structure that causes an increase in the total volume occupied the by the fundus camera, at times making its installation problematic.

To ensure that the infrared light and the light from the Xenon lamp follow the same optical lighting path, beam splitter devices, dichroic mirrors or mechanisms are used, which further complicate the illuminator assembly and increase its costs.

The use of Xenon lamps to generate the flash of white light implies the need to provide high voltage electronic control circuits and, consequently the need to provide adequate electrical insulation, to avoid risks for the user.

Recently, some technical solutions have been proposed which use light sources comprising LED (Light Emitting Diode) devices to supply the light radiation to be projected into the eye of the patient.

In the U.S. Pat. No. 6,142,629 patent, the light coming from a rectangular array of LED devices is collimated, through a cylindrical mirror, towards a linear coupling section, from where it is further transported, through optical fibres, towards an output ring section.

The LED devices forming the rectangular array can emit light with various wavelengths.

A drawback of this technical solution consists in the fact that it is necessary to provide an extensive light emission surface on which to arrange in groups all the LED devices required to emit light with various wavelengths, so as to provide sufficient light power.

This large light emission surface must be optically conjugated with the small useful area for input of light radiation into the optical fibres.

Therefore, it is necessary to use optical systems with high demagnification, thereby causing a considerable increase of the solid angle with which the light is input into the optical fibres.

A solid angle that is too large prevents total reflection of light radiation in the optical fibres, as the useful angle for light input is exceeded. This can cause considerable loss of efficiency of the illuminator, in terms of light power transmitted.

The patent application US2008/0212027 describes a lighting device, in which a ring light source is obtained by providing a plurality of LED devices, close to one another, in the form of a circular ring.

The LED devices are divided in groups to emit light of various wavelengths.

Also in this case, to conjugate the large light emission surface of the LED devices with the small useful area for input of light radiation into the pupil, optical systems with high demagnification must be used.

In the same way described previously, this causes an increase of the solid angle with which the light reaches the pupil.

Taking account of the fact that a fundus camera is normally designed to photograph an area of the retina corresponding to a given solid angle of the incident light (typically 30°-60°), an increase of the solid angle to more than the aforesaid values has the effect of illuminating peripheral areas of the retina not generally observed, but not that of increasing the light power density transmitted to the areas of the retina of interest.

The power density of the light beam generated therefore finds an upper limit in the maximum dimensions available for the light emitting surface.

To increase the light power density on the retina, it is therefore necessary to increase the power density of each LED device, using, for example, LED devices of non-commercial type, produced specifically for this purpose.

Evidently, this causes an increase in the total costs of the illuminator device.

The patent application WO2006/016366 uses a group of LED devices, each of which is coupled to an optical fibre through a lens.

The output ends of the optical fibres are then grouped on a ring-like member to obtain a ring shaped light output section.

This solution allows higher power density values to be reached, even using LED devices of commercial type; however, it is relatively complex and costly to produce at industrial level, given the large number of components to be assembled.

The same patent application also describes the use of single light sources or light sources concentrated on small surfaces, operatively associated with devices to expand the light thus generated, to obtain a ring shaped light output beam.

These light expansion devices comprise, for example, conical or parabolic reflecting surfaces and/or lenses and/or light guide devices, appropriately arranged.

Lighting devices of this type have the disadvantage of using light sources of small dimensions, which are unlikely to be able to offer the power required for flash illumination of the ocular fundus.

A further disadvantage consists in the fact that, to obtain a light beam with selectable wavelength (i.e. infrared and visible), it is necessary to use several emitters coupled by means of dichroic mirrors or mechanisms.

Therefore, these prior art solutions are also structurally complex and costly to produce at industrial level.

The main task of the present invention is to provide a lighting device for fundus cameras which solves the aforesaid problems of prior art.

Within this task, an object of the present invention is to provide a lighting device that ensures a relatively high power density, against smaller angles of divergence of the output light beam emitted, also using LED devices of commercial type to generate the light radiation.

A further object of the present invention is to provide a lighting device that has limited overall dimensions and is easy to install in a fundus camera.

A further object of the present invention is to provide a lighting device that is easy to produce at industrial level, at competitive costs.

This task and these objects, together with other objects that will be more apparent from the subsequent description and from the accompanying drawings, are achieved, according to the invention, by a lighting device according to claim 1, proposed hereunder.

In a further aspect thereof, the present invention also relates to a light concentrator device, according to claim 17, proposed hereunder.

In its more general definition, the lighting device according to the present invention comprises a light source provided with a plurality of LED devices, and a light concentrator device, operatively associated with said light source.

The aforesaid light concentrator device comprises a solid transparent body, preferably made of plastic material.

To receive the light radiation emitted by the light source, a light input section is defined at a first surface of said transparent body.

A light output surface is defined at a second surface of said transparent body to transmit a light beam having a ring shape.

At the input section, the aforesaid transparent body comprises a plurality of protrusions to perform collimation of the light radiation coming from the light source.

The aforesaid transparent body also comprises a plurality of reflection surfaces of the light radiation received from said input section.

These protrusions and these reflection surfaces are mutually positioned so as to convey the light radiation received from said light source along a predefined path, which extends internally to the solid transparent body, between light input section and the light output section.

The use of a light concentrator device according to the present invention makes it possible to obtain a relatively high power density, relatively small angles of divergence and high level of uniformity for the output light beam, to be projected into the patient's eye, also if commercial LED devices are used to generate the light radiation.

The use of a light source, provided with a plurality of LED devices, makes it possible to obtain light beams with different frequencies, whose intensity is easily adjustable through simple electronic control circuits.

The lighting device according to the present invention has relatively limited overall dimensions, making it possible to significantly limit the total volume of the relative fundus camera.

Both the light source and the light concentrator device can be produced with simple industrial processes and easily operatively associated with each other.

The lighting device according to the present invention can therefore be produced and assembled industrially at very competitive costs.

Further characteristics and advantages of the lighting device according to the present invention will be more apparent with reference to the description given below and to the accompanying figures, provided purely for explanatory and non-limiting purposes, wherein:

FIG. 1 schematically illustrates a prior art fundus camera; and

Figure 2:
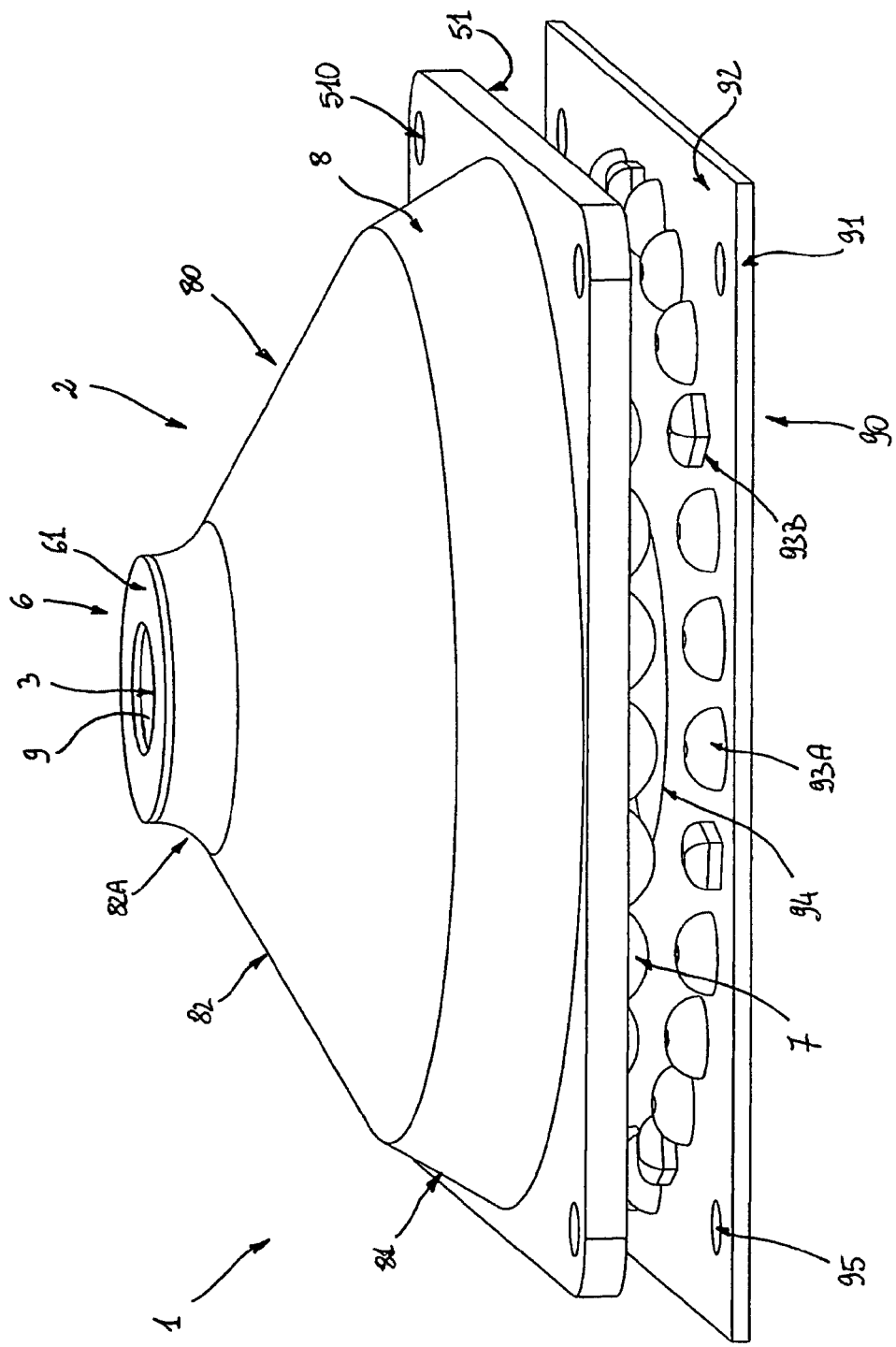
Figure 3:
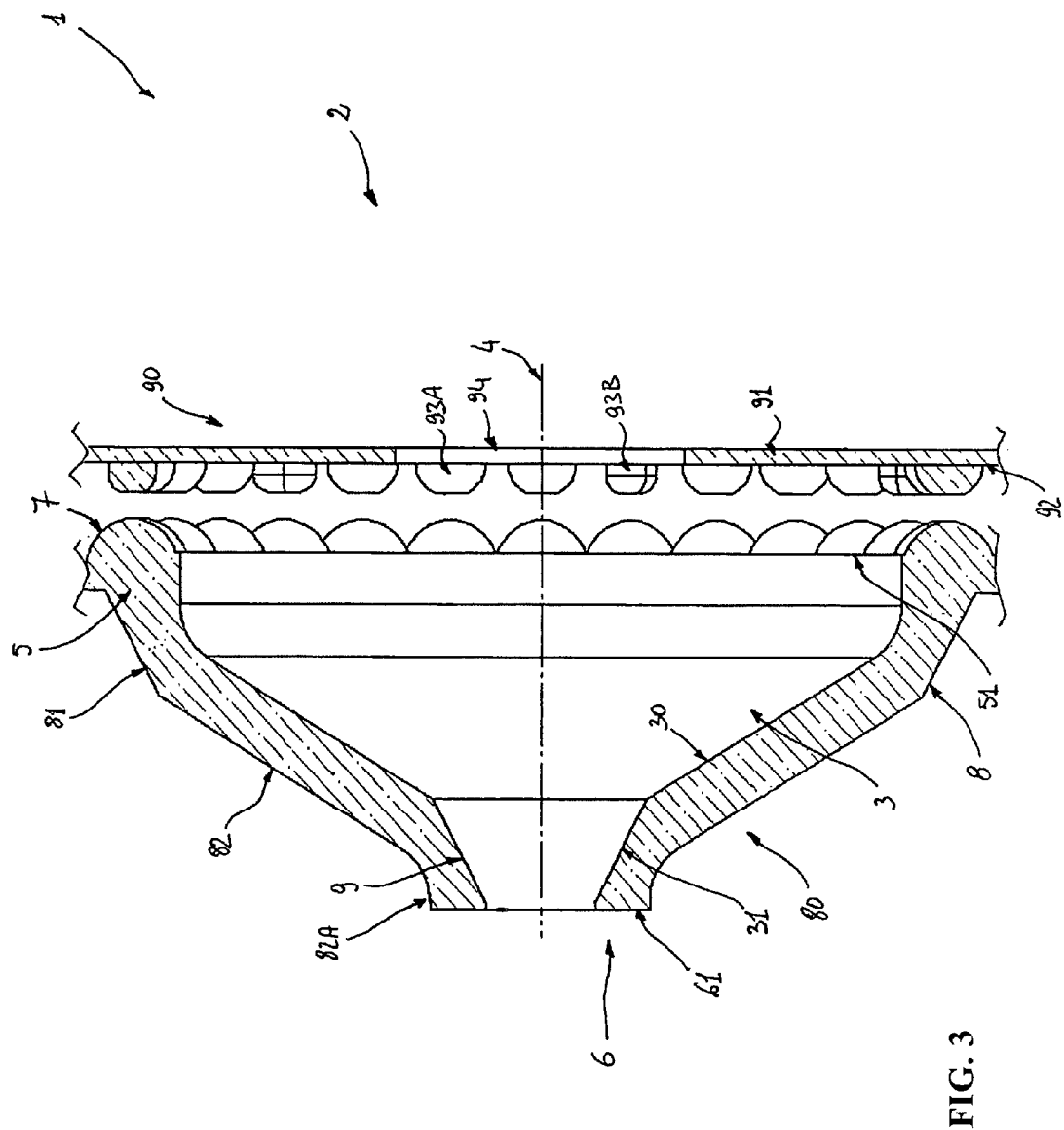
Figure 4:
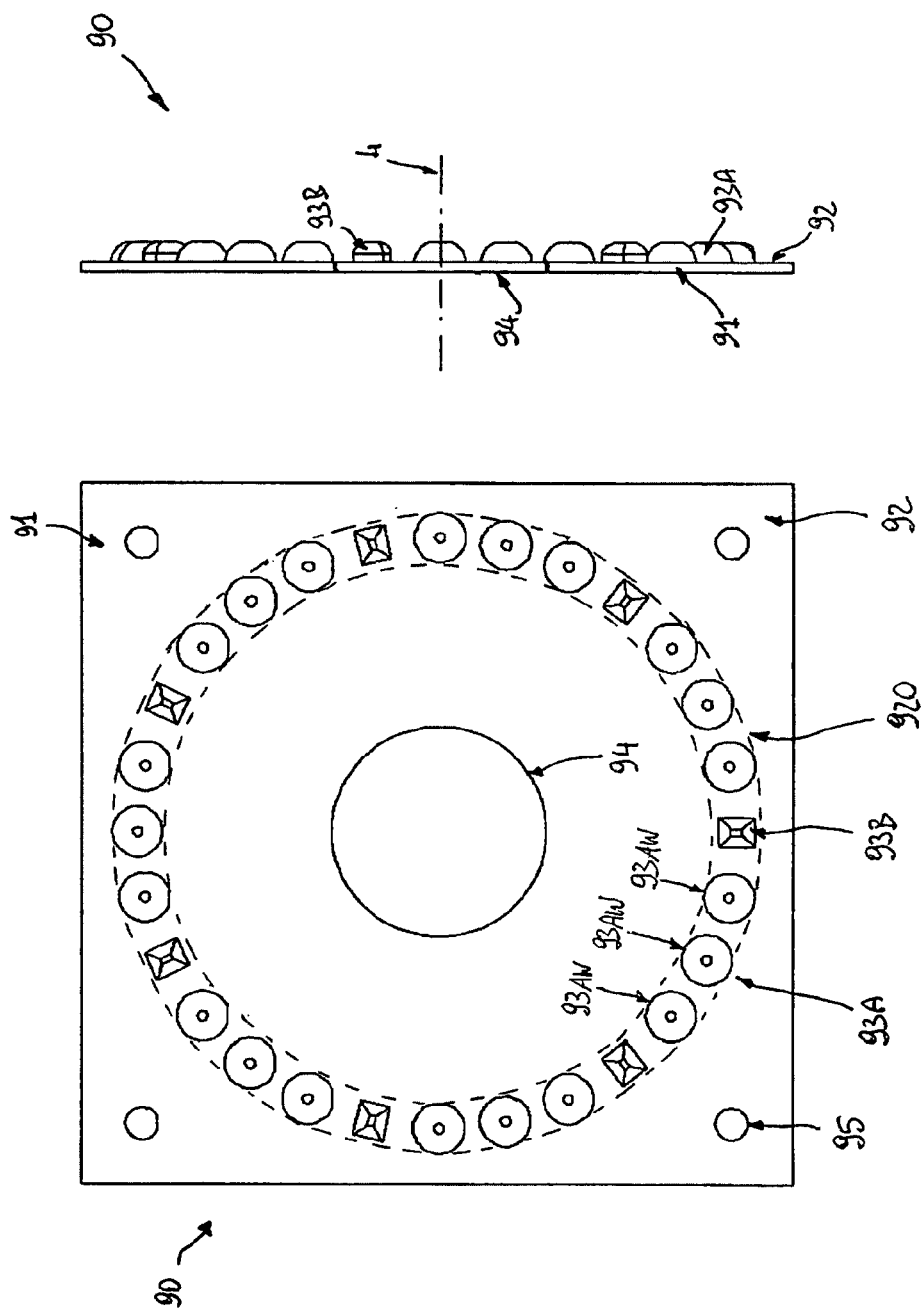
Figure 4A:
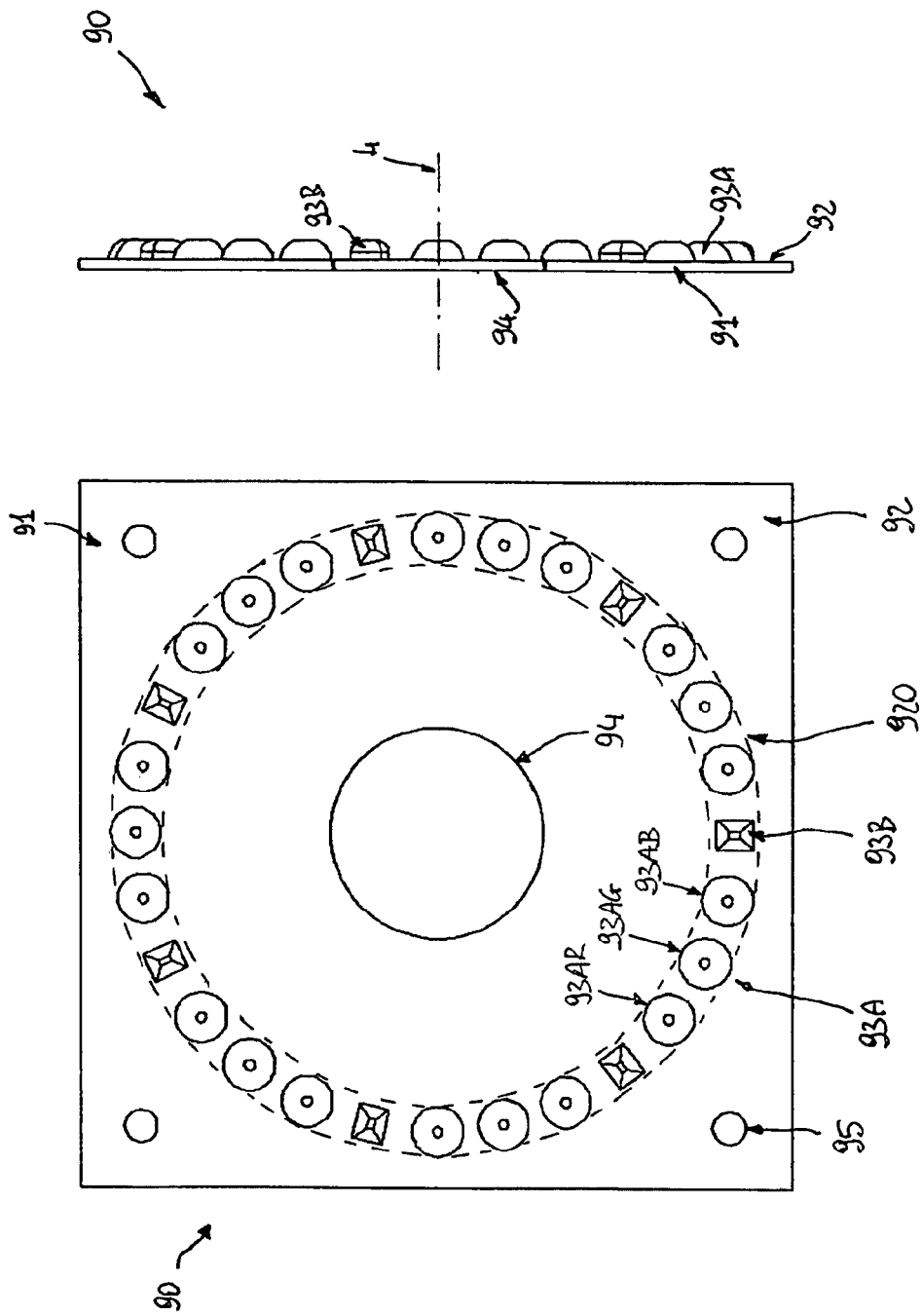
Figure 5:
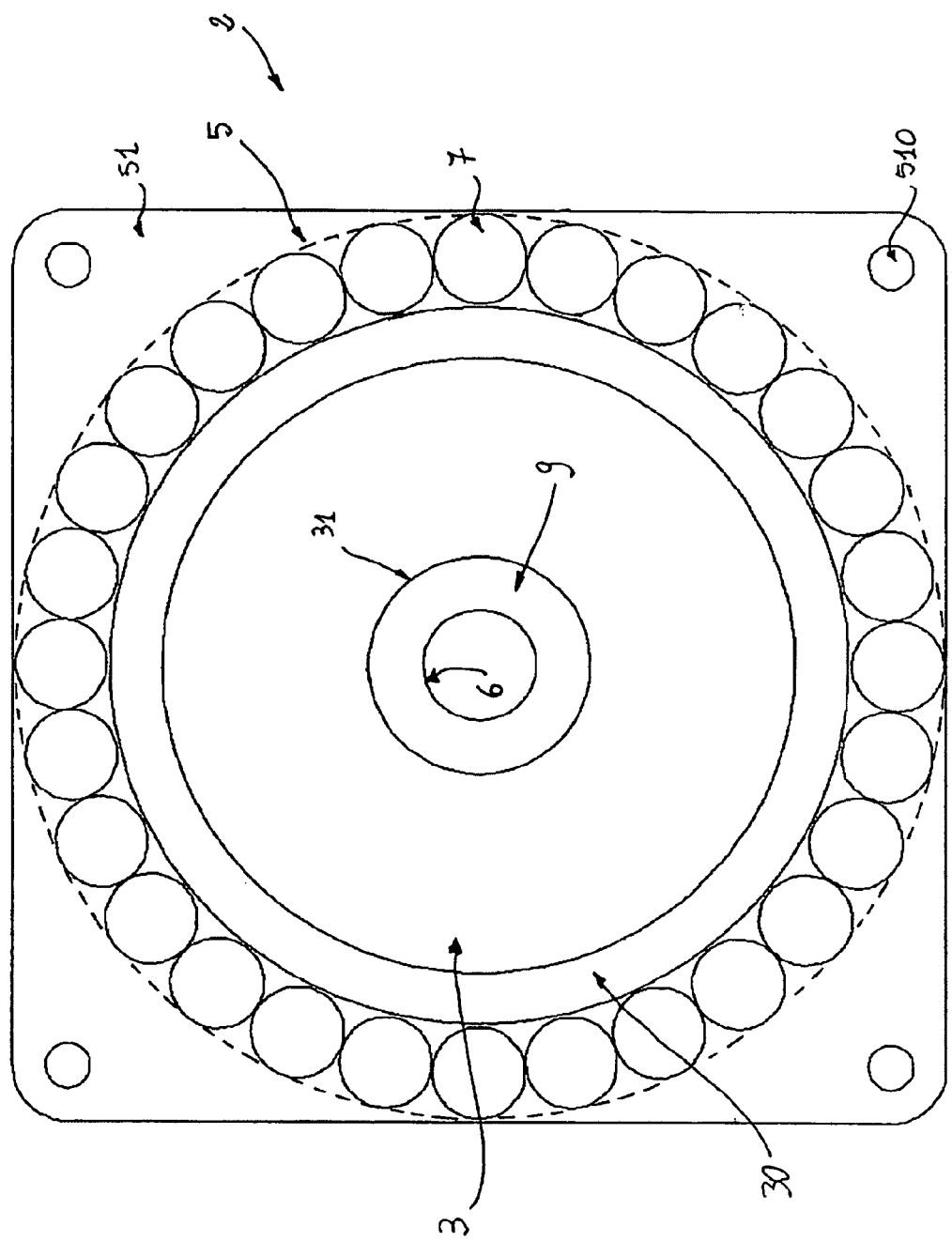
Figure 6:
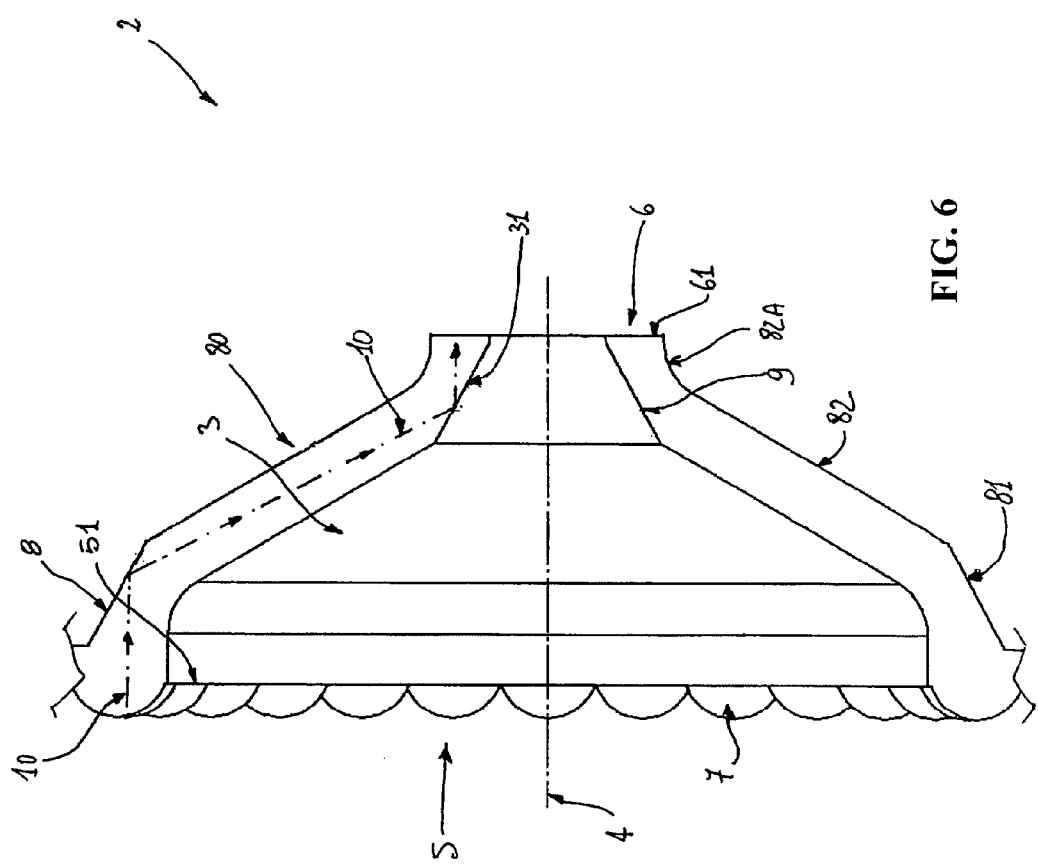
Figure 7:
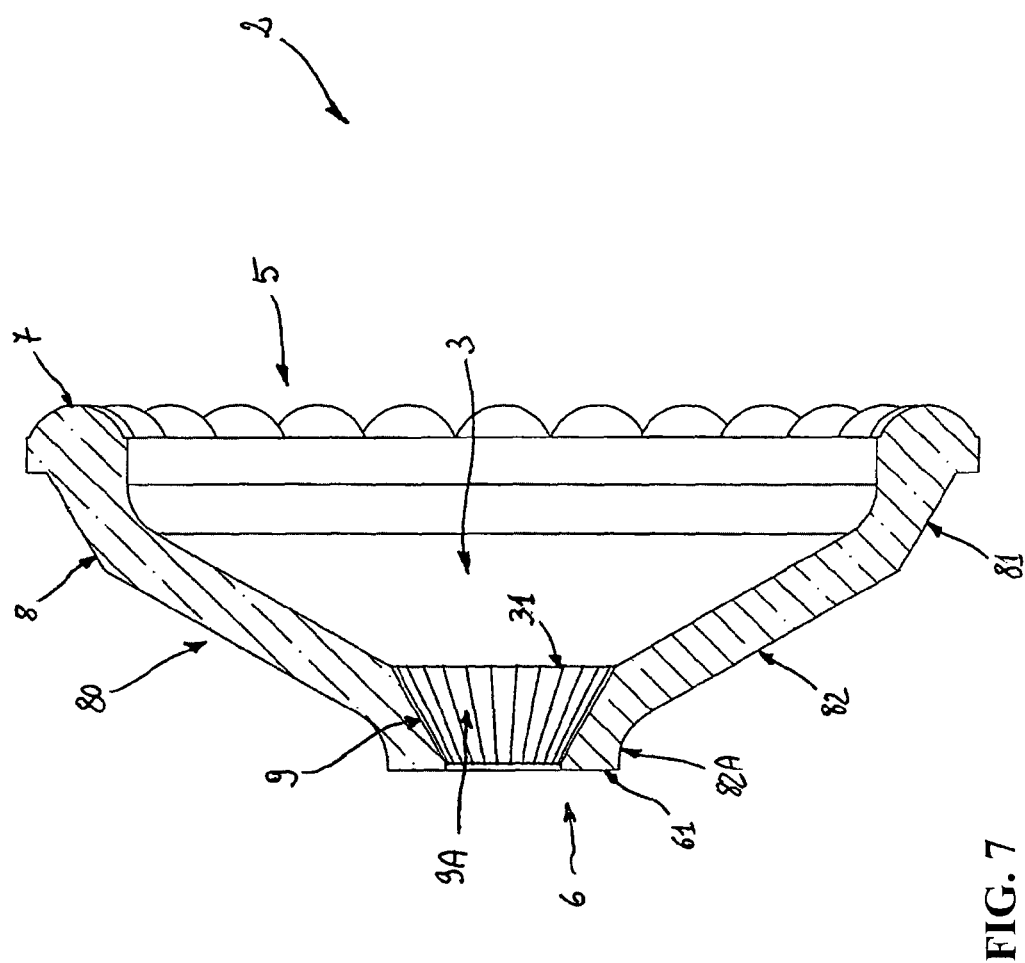
Figure 8:
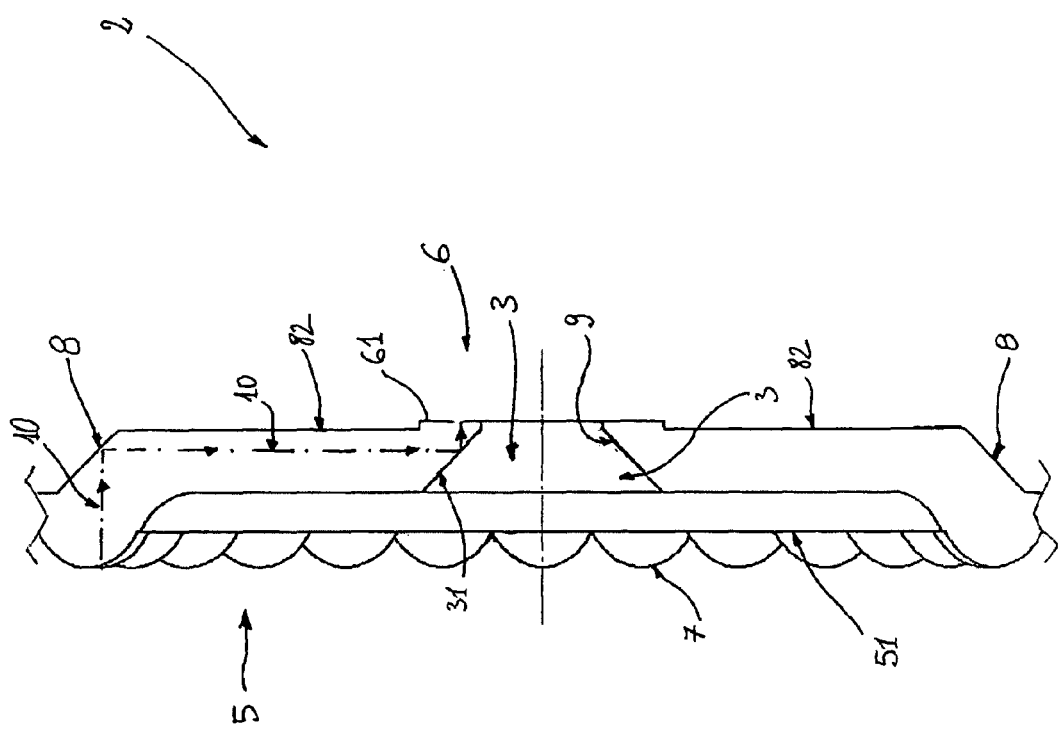

FIG. 2 schematically illustrates a perspective view of the lighting device according to the present invention, in one embodiment thereof; and FIG. 3 schematically illustrates a sectional view of the lighting device of FIG. 2; and FIG. 4 schematically illustrates a side and front view of a light source used in the lighting device of FIG. 1; and FIG. 4A schematically illustrates a side and front view of a light source used in the lighting device of FIG. 1, in a variant of embodiment; and FIG. 5 schematically illustrates a front view of a light concentrator device used in the lighting device of FIG. 1; and FIG. 6 schematically illustrates a sectional view of the light concentrator device of FIG. 5; and FIG. 7 schematically illustrates a sectional view of variant of embodiment of the light concentrator device of FIG. 5; and FIG. 8 schematically illustrates a sectional view of a further variant of embodiment of the light concentrator device of FIG. 5.

With reference to the aforesaid figures, the present invention relates to a lighting device 1 for fundus cameras.

The lighting device 1 comprises a light source 90, which is preferably constituted by a printed circuit board 91 comprising a surface 92, on which a plurality of LED devices 93A, 93B are mounted.

The LED devices 93A and 93B are arranged so as to form a light emitting region 920, which preferably has a substantially ring shape which extends around a cavity 94, produced in the printed circuit 91 and centred with respect to an axis of reference 4.

Advantageously, the light source 90 can comprise differentiated groups 93A and 93B of LED devices, capable of emitting light with different wavelengths.

The groups 93A and 93B can be spaced from one another and arranged along the region 920 according to repeated patterns.

In the embodiment of the invention illustrated in FIG. 4, each group 93A comprises three LED devices 93AW, capable of emitting white light, while each group 93B comprises a single LED device capable of emitting infrared light.

In the embodiment of the invention illustrated in FIG. 4A, each group 93A comprises three LED devices 93AR, 93AG, 93AB, capable of respectively emitting red light, green light and blue light.

This embodiment allows the retina to be illuminated with a light having a given emission spectrum, simply by appropriately controlling the power currents of the LED devices 93AR, 93AG, 93AB.

In this way, it is possible to increase the power of the type of light reflected to a lesser degree from the retina and, conversely, to reduce the power of the type of light reflected to a greater degree from the retina, so that the sensor that detects the image of the retina can operate with an optimal signal/noise ratio for all colours, thereby improving the final quality of the image detected.

The number of LED devices forming each group 93A and 93B can vary as a function of the power required for the different wavelengths.

Preferably, the printed circuit board 91 also comprises electronic control circuits (not illustrated) to adjust the operation and the power supply of the LED devices 93A-93B.

According to the present invention, the lighting device 1 comprises a light concentrator device 2, composed of a solid transparent body, advantageously made of plastic material, by means of known industrial injection moulding processes.

The term "light concentrator device" is intended as a device capable of transmitting output light radiation with a greater power density with respect to that of the input light radiation received.

The transparent body 2 comprises a first surface 51, on which a light input section 5 is defined.

The input section 5 is advantageously adapted to receive the light radiation emitted by the light source 90.

For this purpose, the concentrator device 2 is operatively associated with the light source 90 so that the respective surfaces 51 and 92 are mutually facing and the region 920 is thus optically coupled to the light input section 5.

Advantageously, in order to avoid dispersion of light radiation, the distance between the surfaces 51 and 92 is relatively small and the shape of the region 920 corresponds substantially to the shape of the input section 5, preferably ring shaped.

The transparent body 2 also comprises a surface 61, on which a light output section 6 is defined, from which a ring shaped light beam is emitted.

Advantageously, the output section 6 has a useful area for the passage of light radiation that is smaller with respect to that of the input section 5, so that the power density of the output light transmitted is greater with respect to that of the input light received.

Given that the light input and output sections 5-6 in the transparent body 2 preferably have a substantially ring shape, centred with respect to the longitudinal axis of reference 4, the diameter of the light emitting region 920 is, preferably, substantially equal to the diameter of the input section 5, while the output section 6 has a smaller diameter with respect to the input section 5.

At least close to the second surface 61, the transparent body 2 preferably comprises a shaped cavity 3.

This cavity is preferably a through cavity and extends between the surfaces 51 and 61, along the longitudinal axis 4.

The internal surface of the cavity 3 can be shaped according to needs with the exception of at least a portion 31, positioned close to the output section 6, which preferably has a substantially conical profile.

For reasons of symmetry and constructional simplicity, the output section 6, the input section 5 and the light emission region 920 are advantageously parallel to one another, perpendicular to the longitudinal axis of reference 4 and coaxial with respect thereto.

Moreover, the light source 90 and the transparent body 2 are preferably operatively associated with each other so that the cavity 94 of the printed circuit board 91 is coaxial with the cavity 3 of the transparent body 2, along the axis of reference 4.

According to the present invention, the transparent body 2 comprises a plurality of protrusions 7 acting as collimation lenses of the light radiation coming from the light source 90.

The protrusions 7 protrude from the surface 51 of the transparent body 2, at the input section 5, so as to receive the light generated by the LED devices and collimate it in light beams substantially parallel to the axis of reference 4 (or perpendicular to the surface 51 of the transparent body).

The surface 92 of the light source 90 is advantageously facing the surface 51 of the transparent body 2, so that each of the protrusions 7 is facing and optically coupled to a LED device.

The light radiation emitted by a LED device can thus become a light beam with minimum divergence, after passage through the respective protrusion 7 with which the aforesaid LED device is associated.

Advantageously, the protrusions 7 are equidistant from one another and in a number equal to the number of LED devices of the light source 90, as illustrated in the aforesaid figures.

In this case, the assembly of the aforesaid protrusions 7 can itself form the light input section 5.

Alternatively, the protrusions 7 can be associated with predefined groups of LED devices (i.e. only with the groups 93A) and not be present in the portions of the input section 5 facing groups of different types (i.e. with the groups 93B).

The number of the protrusions 7 can thus be fewer with respect to the total number of LED devices.

The protrusions 7 can have a convex profile of spherical type, a convex profile of aspherical type, designed to improve collimation of the light coming from the LED devices, or a profile with a series of concentric ring sections forming, as a whole, a Fresnel lens.

The transparent body 2 also comprises a plurality of reflection surfaces 8-9 of the light radiation deviated by the protrusions 7.

The protrusions 7 and the reflection surfaces 8-9 are mutually positioned so as to convey the light radiation, coming from the light source 90, along a predefined path 10 which extends through the transparent body 2, between the light input section 5 and the light output section 6.

In other words, the protrusions 7 and the reflection surfaces 8-9 are arranged so as to cooperate with one another to guide the light radiation, coming from the light source 90, and received by the input section 5, towards the output section 6 of the transparent body 2.

Preferably, the transparent body 2 comprises a first surface 8 performing a first reflection of the light radiation deviated by the protrusions 7.

The surface 8 preferably has a substantially conical profile, with mean radius corresponding approximately to that of the input section 5.

The inclination of the conical surface 8 is advantageously selected so that the collimated light radiation, coming from the protrusions 7, undergoes total reflection, so as to change the direction thereof orienting it towards a second reflection surface 9.

It must be noted that in the journey towards the surface 9, the light beams coming from the LED devices and collimated through the protrusions 7 substantially maintain their collimation, even after reflection on the surface 8, which is curved with a relatively high radius.

Advantageously, the path from the surface 8 to the surface 9 can thus be delimited by surfaces 30 and 82 substantially parallel to the directions of the light beams.

In this way, the marginal rays of the light beams are guided through total reflections on the surfaces 30 and 82 to the surface 9 thus reducing the dispersion of light radiation in unwanted directions.

On the surface 9, the light radiation, deviated by the surface 8, undergoes a second total reflection and is deviated towards the output section 6, in a direction substantially parallel to that of the axis of reference 4.

The surface 9 can advantageously coincide with at least a portion 31 of the internal surface of the cavity 3, which is positioned close to the output section 6.

As illustrated in the aforesaid figures, the reflection surface 9 preferably has a substantially conical profile, centred with respect to the axis of reference 4, with mean diameter approximately equal to the mean diameter of the output section 6 of the light radiation.

The light radiation, deviated from the surface 9, thus maintains the collimation in radial direction, i.e. perpendicular to the axis of reference 4, and becomes divergent in tangential direction, i.e. tangent to the mean circle of the ring shaped output surface 6.

The enlargement of the reflected light beams, in tangential direction, has the advantage of creating a greater overlapping between these, improving the homogeneity of the ring shaped beam emitted from the output section 6.

A greater divergence of the output light beam however has the disadvantage of causing a decrease in the total transport efficiency of the light towards the pupil of the patient's eye.

According to a further embodiment of the present invention (FIG. 7) the second reflection surface 9 can have a substantially conical profile comprising a plurality of equidistant faces 9A, preferably of the same number as the total number of LED devices 93A and 93B.

These faces behave as flat mirrors which maintain collimation of the light radiation following reflection on the surface 9.

In this way, it is possible to reduce the divergence of the ring shaped beam emitted from the light output section 6.

The same output section 6 can have a smooth or rough surface, if wishing to further improve respectively the power density or the homogeneity of the light beam to send to the retina.

The transparent body 2 is advantageously configured so as to have a shaped external surface 80 which joins the surfaces 51 and 61.

The external surface 80 comprises a first portion 81, close to the light input section 5, and a second portion 82 which extends between the aforesaid first portion 81 and the surface 61.

Preferably, the reflection surface 8 coincides at least partially with the first portion of external surface 81, which thus has a substantially conical shape.

According to an embodiment of the present invention (FIG. 8), the second portion 82 of external surface is substantially planar, with the exception of an optional connecting area 82A with the surface 61, and has the shape of a circular ring positioned around the surface 61, at which the light output section 6 is defined.

In this case, the transparent body 2 is substantially in the form of a substantially disk-shaped solid, coaxial with the axis of reference 4 and having a base surface formed by the surface 51, a further base surface formed by the surfaces 82 and 61 and a lateral surface formed by the surface 81.

This solution has the advantage of reducing the overall axial dimension of the transparent body 2 and of simplifying the structure of the moulds for its production at industrial level.

The mean angle of reflection of the light radiation on the surfaces 8 and 9 is however maintained relatively high (around 45°). This could prevent total reflection for infrared wavelengths, for which the refraction index of the transparent material decreases.

In this case, therefore, it is preferable to coat the reflection surfaces 8 and 9 with at least a layer of reflecting metallic material, in order to improve the reflection efficiency of the light radiation.

According to some embodiments of the present invention (FIGS. 1-7), the second portion 82 of external surface is substantially conical, with the exception of an optional connecting area 82A with the surface 61.

In this case, the transparent body 2 is in the form of a solid with a substantially truncated-cone shape which extends along the axis of reference 4, with the surfaces 51 and 61 as bases and the portions of external surface 81 and 92 forming the lateral surface thereof.

In this variant of embodiment of the transparent body 2, the angles of incidence of light radiation on the reflection surfaces 8 and 9 can have values that are much lower than the total angle of reflection, eliminating the need to metallise the surface 8 and 9.

This solution, moreover, allows structural strengthening of the transparent body 2, which is consequently less subject to deformations caused by shrinkage of the material during the cooling step following the injection moulding process.

The lighting device 1 according to the present invention has a relatively simple structure, which can be obtained by assembling the light source 90 with the light concentrator device 2, by means of appropriate screws and spacers inserted in the mounting holes 95, 510, produced respectively on the surface 92 of the light source 90 and on the surface 51 of the transparent body 2.

As already mentioned, during mounting of the lighting device 1, the hole 94 of the printed circuit board 91 is advantageously aligned with the cavity 3 of the light concentrator device 2, so that both are coaxial with the axis of reference 4.

Through this coaxial cavity, it is possible if necessary to project light beams inside the eye to be used for a focusing system of the fundus camera.

In prior art, the projection of focusing light beams along the illumination path of the eye is achieved using beam splitter devices or through mirror mechanisms.

However, the projection of focusing light beams through the coaxial cavities 94 and 3 does not require any additional means to be provided, thus allowing simplification of the structure of the fundus camera, reducing the production costs thereof.

The illumination device 1 according to the invention has considerable advantages with respect to prior art.

It allows the transmission of output light beams with high power density and small divergence angles also using commercial LED devices which can optionally emit light with various wavelengths.

The light beams, coming from the LED devices, partially overlap during output from the concentrator device 2, producing a high level of light uniformity for the output light beam.

This light uniformity can be easily improved by increasing the surface roughness of the output section 6, so that this latter performs the function of optical diffuser for the light passing therethrough.

Collimation of the light of the LED devices, by means of the reflection surfaces 7, and conveying of the light radiation from the relatively large input section 5 to the small output section 6 are achieved using a single transparent body, preferably obtained by means of injection moulding and, consequently, with very low production costs.

The light concentrator device 2 has a high transmission efficiency of the light generated by the LED devices, a high level of mechanical sturdiness and does not require adjustments.

The dimensions of the light concentrator device 2 are very limited, allowing a reduction in the overall dimension of the lighting device 1 and of the relative fundus camera.

The lighting device 1 makes it possible to obtain, through the light concentrator device 2, output power densities comparable with those generated by a flash of white light. It is therefore possible to replace the high voltage electronic circuits required to control a Xenon lamp with simpler control circuits for low voltage LED devices.

This obviously causes a reduction in the risk of electric shock for the users, allows the electrical insulation distances between the various components to be reduced and eliminates the need to subject the fundus camera to specific tests for high voltage machinery.

As is evident from the description above, the lighting device 1 has an extremely simple structure. All its parts are easy to produce at industrial level through known processes, with considerable advantages in terms of limiting industrial production costs.

The invention claimed is:

1. A lighting device for a fundus camera comprising:
   a light source-provided with a plurality of LED devices that emit light in a direction substantially perpendicular to a surface on which the LED devices are mounted;
   a light concentrator device, which is operatively associated with said light source, said light concentrator device comprising a solid transparent body that comprises:
      a first surface facing the surface on which said LED devices are mounted, at which a light input section is defined to receive the light radiation emitted by said light source; and
      a second surface, at which a light output section is defined to transmit a light beam having a ring shape, said light output section being smaller than said light input section; and
      a plurality of protrusions that protrude from said first surface, at said light input section, said protrusions acting as collimation lenses of the light radiation coming from said light source; and
      a plurality of reflection surfaces of the light radiation received from said light input section, said protrusions and said reflection surfaces being mutually positioned so as to convey the light radiation coming from said light source along a predefined path, which extends internally to said transparent body, between said light input section and said light output section.

2. A lighting device, according to claim 1, wherein said light source and said transparent body are mutually associated so that each of said protrusions faces a LED of said light source.

3. A lighting device, according to claim 1, wherein said protrusions have a spherical convex profile or an aspherical convex profile or a profile comprising a series of ring sections forming a Fresnel lens.

4. A lighting device, according to claim 1, wherein said transparent body comprises a first reflection surface of the light radiation coming from said light input section, and a second reflection surface of the light radiation deviated by said first reflection surface.

5. A lighting device, according to claim 4, wherein said first reflection surface has a substantially conical profile.

6. A lighting device, according to claim 4, wherein said second reflection surface has a substantially conical profile.

7. A lighting device, according claim 6, wherein said second reflection surface has a substantially conical profile comprising a plurality of faces.

8. A lighting device, according to claim 1, wherein said transparent body comprises a shaped external surface, which extends between said first surface and said second surface, said external surface comprising a first portion, which is close to said first surface, and a second portion, which extends between said first portion and said second surface, said first reflection surface being comprised in the first portion of said external surface.

9. A lighting device, according to claim 8, wherein the second portion of said external surface has a substantially planar shape, at least partially.

10. A lighting device, according to claim 9, wherein said transparent body comprises a first reflection surface of the light radiation coming from said light input section, and a second reflection surface of the light radiation deviated by said first reflection surface and wherein said first reflection surface and said second reflection surface are coated by at least a layer of reflecting metallic material.

11. A lighting device, according to claim 8, wherein the second portion of said external surface has a substantially conical shape, at least partially.

12. A lighting device, according to claim 1, wherein said transparent body comprises a cavity, which is positioned at least close to said second surface.

13. A lighting device, according to claim 12, wherein said transparent body comprises a first reflection surface of the light radiation coming from said light input section, and a second reflection surface of the light radiation deviated by said first reflection surface and wherein said second reflection surface is comprised in at least a portion of an internal of said cavity, which is positioned at least close to said light output section.

14. A lighting device, according claim 1, wherein said light source comprises a light emitting region, said light emitting region having a substantially ring shape, which substantially corresponds to the shape of said light input section.

15. A lighting device, according to claim 1, wherein said light output section has a surface roughness that is sufficiently high to perform the function of optical diffuser for the light passing through said light output section.

16. A fundus camera wherein it comprises a lighting device, according to claim 1.

17. A light concentrator device for fundus cameras wherein it comprises a solid transparent body comprising:

a first surface, at which a light input section is defined to receive the light radiation emitted by a light source provided with a plurality of LED devices, said LED devices being mounted on a surface facing said first surface and emitting light in a direction perpendicular to the surface on which the LED devices are mounted; and a second surface, at which a light output section is defined to transmit a light beam having a ring shape, said light output section being smaller than said light input section; and a plurality of protrusions that protrude from said first surface, at said light input section, said protrusions being acting as collimation lenses of the light radiation coming from said light source; and a plurality of reflection surfaces of the light radiation received from said light input section, said protrusions and said reflection surfaces being mutually positioned so as to convey the light radiation coming from said light source along a predefined path, which extends internally to said transparent body, between said light input section and said light output section.

18. A lighting device, according to claim 2 wherein said protrusions have a spherical convex profile or an aspherical convex profile or a profile comprising a series of ring sections forming a Fresnel lens.

19. A lighting device, according to claim 2, wherein said transparent body comprises a first reflection surface of the light radiation coming from said light input section, and a second reflection surface of the light radiation deviated by said first reflection surface.

20. A lighting device, according to claim 3, wherein said transparent body comprises a first reflection surface of the light radiation coming from said light input section, and a second reflection surface of the light radiation deviated by said first reflection surface.

* * * * *